| United States Patent [19] | [11] Patent Number: 4,806,530 |
| Langer | [45] Date of Patent: Feb. 21, 1989 |

[54] PHARMACEUTICAL COMPOSITIONS BASED ON DILTIAZEM AND LYSINE ACETYLSALICYLATE

[75] Inventor: Salomon Langer, Paris, France

[73] Assignee: Synthelabo, France

[21] Appl. No.: 111,151

[22] Filed: Oct. 21, 1987

Related U.S. Application Data

[63] Continuation of Ser. No. 888,078, Jul. 22, 1986, abandoned.

[30] Foreign Application Priority Data

Jul. 30, 1985 [FR] France .................................. 85 11603

[51] Int. Cl.$^4$ ............................................. A61K 31/62

[52] U.S. Cl. ..................................................... 514/161
[58] Field of Search ......................................... 524/161

[56] References Cited

PUBLICATIONS

Chem. Abst., 85-137445b (1976).
Chem. Abst., 92-51880u (1980).
Chem. Abst., 98-212475g (1983).

*Primary Examiner*—Stanley J. Friedman
*Attorney, Agent, or Firm*—Wegner & Bretschneider

[57] ABSTRACT

Pharmaceutical composition containing both diltiazem and lysine acetylsalicylate exhibits enhanced platelet aggregation inhibitory properties.

1 Claim, No Drawings

PHARMACEUTICAL COMPOSITIONS BASED ON DILTIAZEM AND LYSINE ACETYLSALICYLATE

This application is a continuation of U.S. application Ser. No. 888,078, filed July 22, 1986, now abandoned.

The present invention relates to pharmaceutical compositions based on diltiazem and lysine acetylsalicylate, the compositions being intended for use in the treatment of platelet aggregation.

Diltiazem or cis(+)-3-acetyloxy-5-[2-dimethylamino)ethyl]-2,3-dihydro-2-(4-methoxy phenyl)-1,5-benzothiazepin-4(5H)-one of formula

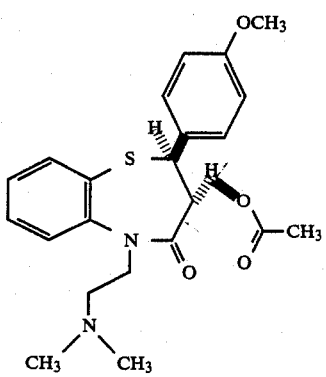

is known for its antianginal, antihypertensive, calcium antagonistic and platelet aggregation inhibitory activities.

Lysine acetylsalicylate (LAS), of formula

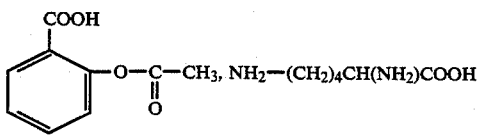

is known for its analgesic, anti-inflammatory and platelet aggregation inhibitory properties.

I have found that, surprisingly, the platelet aggregation inhibitory properties of each of these compounds are potentiated when the two compounds are used together.

The pharmaceutical compositions of the invention were subjected to a series of pharmacological trials.

The compositions were tested in vitro in the following manner:
the compounds are administered, either alone or in combination, to a suspension of platelets and plasma present in the 250-µl cells of an aggregometer, two minutes before adding 10 µg of arachidonic acid, an agent which induces platelet aggregation. The aggregation is followed in a twin-channel chronological aggregometer according to the method of Born, Journal of Physiology, 168, 178-195 (1963).

The results obtained are given in Tables 1 and 2.

TABLE 1

| Concentration of LAS µM | Concentration of diltiazem µM | % inhibition of platelet aggregation | | |
|---|---|---|---|---|
| | | LAS alone | Diltiazem alone | LAS + diltiazem |
| 10 | 200 | 6 | 3 | 88 |
| 20 | 200 | 13 | 12 | 66 |
| 50 | 200 | 25 | 9 | 72 |
| 50 | 200 | 9 | 6 | 79 |
| 20 | 400 | 7 | 27 | 96 |
| 50 | 400 | 9 | 27 | 100 |

LAS = lysine acetylsalicylate.

TABLE 2

| Concentration of diltiazem µM | Concentration of LAS µM | % inhibition of platelet aggregation | | |
|---|---|---|---|---|
| | | Diltiazem alone | LAS alone | Diltiazem + LAS |
| 200 | 10 | 3 | 6 | 88 |
| 200 | 20 | 12 | 13 | 66 |
| 400 | 20 | 27 | 7 | 96 |
| 200 | 50 | 9 | 25 | 72 |
| 400 | 50 | 27 | 9 | 100 |

The compositions of the invention were tested in vivo in the following manner:
diltiazem at a dose of 10 mg/kg and LAS at a dose of 1 mg/kg are administered orally, either alone or in combination, to five groups of two rats. After one hour, blood samples are drawn. Suspension of plasma and platelets are then prepared and placed in the 250-µl cells of an aggregometer two minutes before adding arachidonic acid (200-250 µg/ml). The aggregation is followed in a twin-channel chronological aggregometer according to the method of Born.

The results are given in Table 3.

TABLE 3

| Dose of LAS mg/kg p.o. | Dose of diltiazem mg/kg p.o. | % inhibition of platelet aggregation (mean of 5 experiments) | | |
|---|---|---|---|---|
| | | LAS alone | Diltiazem alone | LAS + diltiazem |
| 1 | 10 | 8 | 9 | 81 |

Results show that the combination of lysine acetylsalicylate and diltiazem produces a platelet aggregation inhibitory effect which is significantly larger than the sum of the effects engendered by each of the compounds administered separately.

There is potentiation of the platelet aggregation inhibitory activity of each of the compounds, LAS and diltiazem, by the other.

The pharmaceutical compositions of the invention can contain from 3 to 60 mg of diltiazem and from 10 to 300 mg of LAS per unit dose.

The pharmaceutical compositions of the invention can be presented in any form suitable for oral or parenteral administration, in combination with any suitable excipient.

The pharmaceutical compositions of the invention can be used for the treatment of coronary and cerebrovascular thrombosis, peripheral vascular conditions, disorders of platelet aggregation and migraine.

The daily dosage can be from 2 to 3 unit doses.

I claim:

1. A pharmaceutical composition which contains from 3 to 60 mg of diltiazem and from 10 to 300 mg of lysine acetylsalicylate per unit dose.

* * * * *